US012778889B2

(12) United States Patent
Shimoyama et al.

(10) Patent No.: US 12,778,889 B2
(45) Date of Patent: Nov. 3, 2026

(54) LIPOSOME COMPOSITION CONTAINING TOPOTECAN FOR TREATING MERKEL CELL CANCER

(71) Applicant: FUJIFILM Corporation, Tokyo (JP)

(72) Inventors: Susumu Shimoyama, Cambridge, MA (US); Mikinaga Mori, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 84 days.

(21) Appl. No.: 18/516,010

(22) Filed: Nov. 21, 2023

(65) Prior Publication Data

US 2024/0099974 A1 Mar. 28, 2024

Related U.S. Application Data

(63) Continuation of application No. PCT/JP2022/021106, filed on May 23, 2022.

(60) Provisional application No. 63/192,329, filed on May 24, 2021.

(51) Int. Cl.

| | |
|---|---|
| ***A61K 9/127*** | (2025.01) |
| ***A61K 9/00*** | (2006.01) |
| ***A61K 9/1271*** | (2025.01) |
| ***A61K 31/4745*** | (2006.01) |
| ***A61K 33/04*** | (2006.01) |
| ***A61P 35/00*** | (2006.01) |

(52) U.S. Cl.

CPC .......... *A61K 9/1271* (2013.01); *A61K 9/0019* (2013.01); *A61K 31/4745* (2013.01); *A61K 33/04* (2013.01); *A61P 35/00* (2018.01)

(58) Field of Classification Search

None

See application file for complete search history.

(56) References Cited

U.S. PATENT DOCUMENTS

| | | | | |
|---|---|---|---|---|
| 6,355,268 | B1 | 3/2002 | Slater et al. | |
| 7,060,828 | B2 | 6/2006 | Madden et al. | |
| 7,811,602 | B2 | 10/2010 | Cullis et al. | |
| 11,413,244 | B2 | 8/2022 | Kasagi et al. | |
| 2007/0117832 | A1* | 5/2007 | Dell'orco | A61P 35/00 546/51 |
| 2009/0285878 | A1 | 11/2009 | Hope et al. | |
| 2020/0016079 | A1 | 1/2020 | Kasagi et al. | |
| 2021/0213051 | A1 | 7/2021 | Okada et al. | |

FOREIGN PATENT DOCUMENTS

| | | | | |
|---|---|---|---|---|
| CN | 110505869 A | | 11/2019 | |
| CN | 112789032 A | | 5/2021 | |
| JP | 2008-519045 A | | 6/2008 | |
| JP | 2010-518140 A | | 5/2010 | |
| WO | 2018/181963 A1 | | 10/2018 | |
| WO | WO-2019244979 A1 | * | 12/2019 | A61K 9/1271 |
| WO | 2020/071349 A1 | | 4/2020 | |

OTHER PUBLICATIONS

Rabinowits (OncoTargets and Therapy 10, 4803-4807) Is this the end of cytotoxic chemotherapy in Merkel cell carcinoma? (Year: 2017).*

International Search Report (PCT/ISA/210) dated Aug. 9, 2022 issued by the International Searching Authority in International Application No. PCT/JP2022/021106.

Written Opinion (PCT/ISA/237) dated Aug. 9, 2022 issued by the International Searching Authority in International Application No. PCT/JP2022/021106.

International Preliminary Report on Patentability (with translation of Written Opinion) dated Nov. 21, 2023, issued in International Application No. PCT/JP2022/021106.

Dresang, L. R., et al., "Response of Merkel Cell Polyomavirus-Positive Merkel Cell Carcinoma Xenografts to a Survivin Inhibitor", PLos One, Nov. 2013, vol. 8, Issue 11, pp. 1-14.

Mould, D., et al., "Population pharmacokinetic and adverse event analysis of topotecan in patients with solid tumors", Clinical Pharmacology & Therapeutics, vol. 71, No. 5, May 2002, pp. 334-348.

Ait-Oudhia, S., et al., "Application of Pharmacokinetic and Pharmacodynamic Analysis to the Development of Liposomal Formulations for Oncology", Pharmaceutics, 2014, vol. 6, pp. 137-174.

Hycamtin™ Prescribing Information, Novartis, Revised Oct. 2019, 15 pages total.

Extended European Search Report dated Aug. 2, 2024 in European Application No. 22811285.0.

Matulonis et al, "A first in human phase 1 dose escalation study of FF-10850 (liposomal topotecan) in patients with advanced solid tumors", Journal of Clinical Oncology, Jun. 1, 2022, vol. 40, (2 pages).

Communication dated Dec. 23, 2025, issued in Taiwanese Application No. 111119107.

Communication dated Jan. 19, 2026, issued in Chinese application No. 202280036277.2.

Communication dated Apr. 14, 2026, in Japanese Application No. 2023-523467.

Communication dated Apr. 30, 2026, issued in European application No. 22811285.0.

(Continued)

*Primary Examiner* — Tigabu Kassa

(74) *Attorney, Agent, or Firm* — Sughrue Mion, PLLC

(57) ABSTRACT

An object of the present invention is to provide a treatment agent for Merkel cell cancer. According to the present invention, there is provided a treatment agent for Merkel cell cancer, having a liposome which has an inner water phase and having an aqueous solution which is an outer water phase and disperses the liposome, in which the liposome encompasses topotecan or a salt thereof, a lipid constituting the liposome contains a lipid modified with polyethylene glycol, dihydrosphingomyelin, and cholesterol, and the inner water phase contains an ammonium salt.

7 Claims, 1 Drawing Sheet

(56) References Cited

OTHER PUBLICATIONS

Chinese Patent Office, Communication issued Aug. 3, 2026, in Chinese Application No. 202280036277.2, with English translation.
Dresang et al., "Response of Merkel Cell Polyomavirus-Positive Merkel Cell Carcinoma Xenografts to a Survivin Inhibitor", PLOS One, Nov. 18, 2013, vol. 8, Issue 11, pp. 1-14, e80543.
Communication issued Aug. 14, 2026 in Japanese Application No. 2023-523467, with English Translation.

* cited by examiner

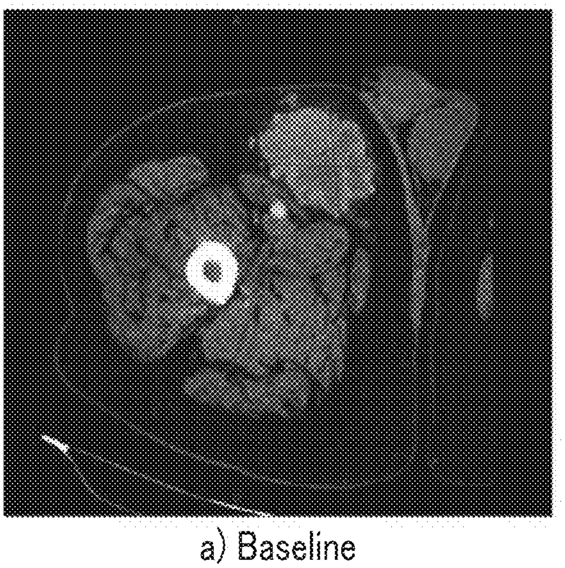
a) Baseline
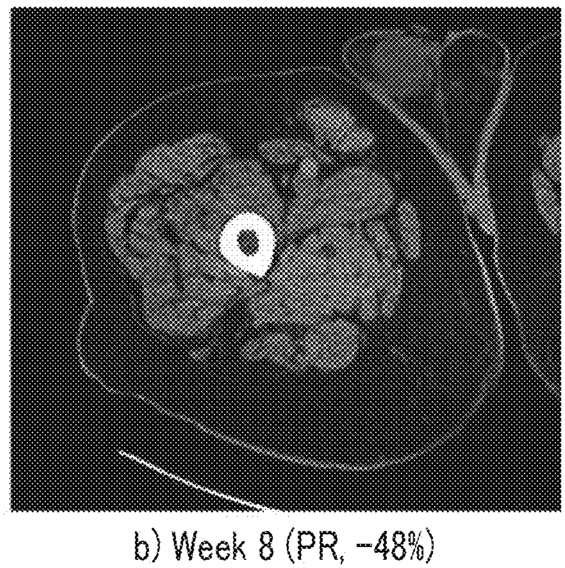
b) Week 8 (PR, −48%)
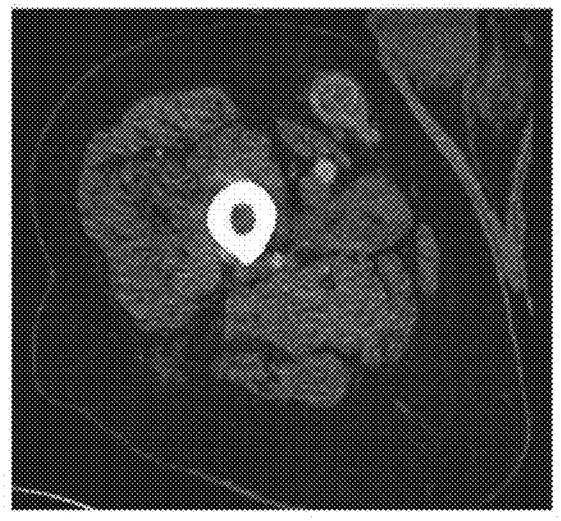
c) Week 16 (Confirmed PR)

LIPOSOME COMPOSITION CONTAINING TOPOTECAN FOR TREATING MERKEL CELL CANCER

CROSS-REFERENCE TO RELATED APPLICATIONS

This application is a Continuation of PCT International Application No. PCT/JP2022/021106 filed on May 23, 2022, which claims priority under 35 U.S.C § 119(a) to U.S. Provisional Application No. 63/192,329 filed on May 24, 2021. Each of the above application(s) is hereby expressly incorporated by reference, in its entirety, into the present application.

BACKGROUND OF THE INVENTION

1. Field of the Invention

The present invention relates to a treatment agent for prevention, curing, or the like of Merkel cell cancer.

2. Description of the Related Art

The Merkel cell cancer is a tumor with a very high degree of malignancy, in which local recurrence, local lymph node metastasis, and distant metastasis occur with high probability, and the prognosis is poor. The first option for the curing thereof is massive resection, and preventive lymph node dissection or radiation therapy is also carried out. An immune checkpoint inhibitor is used in advanced cases in which recurrence or metastasis has occurred. Although various chemotherapy has also been reported, there is no established chemotherapy yet.

On the other hand, in chemotherapy, it is often studied that a drug is accumulated at a disease site such as cancer and exposed thereto over a long period of time by means of a liposome composition.

WO2018/181963 describes that a liposome composition containing a hydrophilic polymer-modified diacylphosphatidylethanolamine, dihydrosphingomyelin, and cholesterols as the constitutional components of the liposome membrane exhibits a high area under the blood concentration-time curve (AUC).

U.S. Pat. No. 7,060,828B2 discloses a liposome in which topotecan is encapsulated in a liposome containing sphingomyelin and cholesterol.

U.S. Pat. No. 7,811,602B2 discloses a liposome in which topotecan is encapsulated in a liposome containing dihydrosphingomyelin and cholesterol.

JP2008-519045A discloses a liposomal camptothecin preparation adapted to enhance the stability of camptothecin, including (a) camptothecin encapsulated in a liposome, (b) first solution which is external to the liposome and has a pH of 4.5 or less than 4.5, and (c) second solution which is internal to the liposome. It is also disclosed that the liposome contains dihydrosphingomyelin and cholesterol.

U.S. Pat. No. 6,355,268B2 discloses a liposome in which topotecan is encapsulated in the presence of ammonium sulfate in a liposome containing purified hydrogenated soybean phospholipid or sphingomyelin, cholesterol, and a hydrophilic polymer derivative lipid.

SUMMARY OF THE INVENTION

As described above, the therapy for the Merkel cell cancer has not been established yet, except for using an immune checkpoint inhibitor, and an effective treatment agent for preventing or curing the Merkel cell cancer is desired.

On the other hand, so far, there has been no report on the result of the administration of liposomes encompassing topotecan or a salt thereof to a cancer patient, and it has not been studied what kind of drug efficacy is exhibited with respect to a cancer patient by the liposomes encompassing topotecan or a salt thereof.

As a result of diligent studies to solve the above problem, the inventors of the present invention found that liposomes encompassing topotecan or a salt thereof are effective in the treatment of Merkel cell cancer, whereby the present invention was completed.

That is, the present invention provides the following aspects.

[1] A treatment agent for Merkel cell cancer, comprising:

a liposome which has an inner water phase; and an aqueous solution which is an outer water phase and disperses the liposome, in which the liposome encompasses topotecan or a salt thereof, a lipid constituting the liposome contains a lipid modified with polyethylene glycol, dihydrosphingomyelin, and cholesterol, and the inner water phase contains an ammonium salt.

[2] The treatment agent according to [1], in which the dihydrosphingomyelin is dihydrosphingomyelin having an alkyl group having 16 carbon atoms and an alkyl group having 18 carbon atoms.

[3] The treatment agent according to [1] or [2], in which the ammonium salt is ammonium sulfate, and a molar ratio of sulfate ions contained in the inner water phase to the molar sum of the topotecan or the salt thereof contained in the treatment agent is 0.36 or more in terms of topotecan.

[4] The treatment agent according to any one of [1] to [3], in which the lipid modified with polyethylene glycol is diacylphosphatidylethanolamine modified with polyethylene glycol or methoxypolyethylene glycol.

[5] The treatment agent according to any one of [1] to [4], in which a formulation ratio of the cholesterol to a total of the lipid constituting the liposome is 35% to 43% by mole.

[6] The treatment agent according to any one of [1] to [5], in which a pH of the outer water phase is 5.5 to 8.5.

[7] The treatment agent according to any one of [1] to [6], in which the topotecan or the salt thereof encompassed in the liposome is administered at a dose rate of 0.1 $mg/m^2$ body surface area to 10 $mg/m^2$ body surface area, in terms of topotecan per administration.

[8] The treatment agent according to any one of [1] to [7], in which a plurality of times of single administration is repeated every one week to eight weeks.

[9] The treatment agent according to any one of [1] to [8], in which an administration route is an intravenous administration.

[A] A method that is a treatment method for Merkel cell cancer, comprising:

a step of administering a composition having a liposome which has an inner water phase and an aqueous solution which is an outer water phase and disperses the liposome, in which the liposome encompasses topotecan or a salt thereof, a lipid constituting the liposome contains a lipid modified with polyethylene glycol, dihydrosphingomyelin, and cholesterol, and the inner water phase contains an ammonium salt.

[B] A treatment agent for being used in treatment of Merkel cell cancer, the treatment agent comprising:

a liposome which has an inner water phase; and an aqueous solution which is an outer water phase and disperses the liposome, in which the liposome encompasses topotecan or a salt thereof, a lipid constituting the liposome contains a lipid modified with polyethylene glycol, dihydrosphingomyelin, and cholesterol, and the inner water phase contains an ammonium salt.

[C] A use of a composition for producing a treatment agent for treating Merkel cell cancer, in which the composition contains;

a liposome which has an inner water phase; and an aqueous solution which is an outer water phase and disperses the liposome, where the liposome encompasses topotecan or a salt thereof, a lipid constituting the liposome contains a lipid modified with polyethylene glycol, dihydrosphingomyelin, and cholesterol, the inner water phase contains an ammonium salt, and the topotecan or the salt thereof encompassed in the liposome is administered at a dose rate of 0.1 $mg/m^2$ body surface area to 10 $mg/m^2$ body surface area, in terms of topotecan per administration.

The treatment agent according to the aspect of the present invention is useful for treatment such as prevention, curing, or the like of Merkel cell cancer. In addition, the effect of reducing the volume of the Merkel cell cancer is remarkable in a case where the treatment agent according to the aspect of the present invention is administered to a subject. In addition, due to the effect obtained by the treatment agent according to the aspect of the present invention, it is expected that the extension of progression-free survival time and overall survival time, the improvement of QOL, and the like are achieved in a subject subjected to administration.

BRIEF DESCRIPTION OF THE DRAWINGS a of FIG. 1 to c of FIG. 1 show CT images in a case where a curing effect on a Merkel cell cancer patient has been confirmed.

DESCRIPTION OF THE PREFERRED EMBODIMENTS

In the present invention, the range represented by "to" includes the values at both ends thereof unless otherwise specified.

The "treatment" means curing or prevention of each disease.

The "subject" is a mammal such as a human, a mouse, a monkey, or a domestic animal requiring prevention or curing therefor, and preferably a human requiring prevention or curing therefor.

The "prevention" means the inhibition of the onset of a disease, the reduction of the risk of the onset of a disease, or the delay of the onset of a disease.

The "curing" means the amelioration or the suppression (the maintenance or delay) of the progression of a disease or state.

The "progression-free survival time" means the time during which cancer has not progressed and remained in a stable state during curing (after curing).

The "overall survival time" means the time during which a subject has survived from the allocation start date of therapy or curing start date in a clinical test "QOL" is an abbreviation for Quality of Life and means a quality of life including all of the physical, spiritual, social, and economic aspects of a subject that leads a life of curing or medical treatment.

Hereinafter, the present invention will be described in detail.

The present invention relates to a treatment agent for Merkel cell cancer, having a liposome which has an inner water phase and having an aqueous solution which is an outer water phase and disperses the liposome, where the liposome encompasses topotecan or a salt thereof, a lipid constituting the liposome contains a lipid modified with polyethylene glycol, dihydrosphingomyelin, and cholesterol, and the inner water phase contains an ammonium salt.

(Liposome)

A liposome is a closed vesicle formed of a lipid bilayer membrane using a lipid, and an aqueous phase (an inner water phase) is included in the space of the closed vesicle. The inner water phase contains water. The liposome is generally present in a state of being dispersed in an aqueous solution (an outer water phase) outside the closed vesicle. The liposome may be a single lamella (which is also called a single-layer lamella or uni-lamella, where the bilayer membrane has a single layered structure) or may be a multi-layer lamella (which is also called a multi-lamella and has a structure of a large number of bilayer membranes, having an onion-like shape, where the individual layers are separated by an aqueous layer). However, in the present invention, a single lamellar liposome is preferable from the viewpoint of safety and stability in pharmaceutical use applications.

The form of the liposome is not particularly limited as long as the liposome is a liposome capable of encompassing a drug. The "encompassing" means taking a form in which a drug is contained in the inner water phase of the liposome. Examples thereof include a form in which a drug is enclosed in a closed space formed of a membrane and a form in which a drug is encompassed in the membrane itself, where a combination of these may be good.

In general, the average particle diameter of the liposome is 10 nm to 1,000 nm, preferably 20 nm to 500 nm, more preferably 30 nm to 300 nm, still more preferably 30 nm to 200 nm, even still more preferably 30 nm to 150 nm, and particularly preferably 50 to 150 nm. The liposome preferably has a spherical shape or a shape close thereto.

In a case of expecting the enhanced permeability and retention effect (the EPR effect), the diameter is preferably substantially 50 to 200 nm, the diameter is more preferably substantially 50 to 150 nm, and the diameter is still more preferably substantially 50 to 100 nm. The term "substantially" means that at least 75% of the number of liposomes is within the specified diameter range. The above-described "at least 75%" is more preferably at least 80% and still more preferably at least 90%.

It is noted that in the present invention, the "average particle diameter" means an average particle diameter (preferably, a cumulant average particle diameter) measured by using a dynamic light scattering method unless otherwise specified. The "average particle diameter" can be measured by using a device that can measure the average particle diameter according to a light scattering method.

The component constituting the lipid bilayer of the liposome is selected from lipids. The liposome in the present invention includes a hydrophilic polymer-modified diacylphosphatidylethanolamine, dihydrosphingomyelin, and cholesterol as the constitutional components of the liposome membrane.

The liposome according to the embodiment of the present invention contains dihydrosphingomyelin. The retention of the liposome in the blood can be improved by using dihydrosphingomyelin. In addition, it is possible to improve the partition properties of the liposome membrane and prevent the leakage of topotecan or a salt thereof.

Dihydrosphingomyelin generally has two long-chain alkyl groups in the molecule, and examples thereof include dihydrosphingomyelin having two long-chain alkyl groups respectively having 16 carbon atoms, dihydrosphingomyelin having a long-chain alkyl group having 16 carbon atoms and a long-chain alkyl group having 18 carbon atoms, and dihydrosphingomyelin having a long-chain alkyl group having 16 carbon atoms and a long-chain alkyl group having 20 to 24 carbon atoms.

From the viewpoint of preventing leakage of a drug from the liposome, it is preferable to use, as the dihydrosphingomyelin, the following compound having a long-chain alkyl group having 16 carbon atoms and a long-chain alkyl group having 18 carbon atoms. This is because the melting point becomes higher as the number of carbon atoms is larger, and therefore a liposome membrane having high partition properties can be formed.

modified sterol. The hydrophilic polymers may be each used alone or in a combination of two or more kinds thereof.

The molecular weight of the polyethylene glycol is not particularly limited and is 500 to 10,000 daltons, preferably 1,000 to 7,000 daltons, and more preferably 2,000 to 5,000 daltons.

Examples of the PEG-modified lipid include 1,2-distearoyl-3-phosphatidylethanolamine-polyethylene glycol such as 1,2-distearoyl-3-phosphatidylethanolamine-PEG2000 (manufactured by NOF Corporation), distearoyl glycerol PEG2000 (manufactured by NOF Corporation), or 1,2-distearoyl-3-phosphatidylethanolamine-PEG5000 (manufactured by NOF Corporation), and cholesterol-polyethylene glycol such as cholesterol-PEG600 (manufactured by Merck KGaA).

From the viewpoint of the general-purpose properties and the blood retention, the PEG-modified lipid is preferably a PEG-modified phospholipid or a PEG-modified monoalkyl ether and is more preferably a PEG-modified phospholipid. Among the PEG-modified phospholipids, PEG-modified phosphatidylethanolamine is preferable, and diacylphosphatidylethanolamine modified with polyethylene glycol or methoxypolyethylene glycol is more preferable.

The ratio of the PEG-modified lipid in the total lipids constituting the liposome is preferably 1% to 15% by mole and more preferably 2% to 10% by mole.

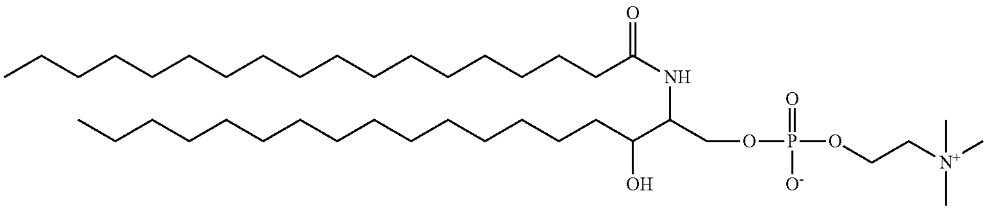 [SMILES: CCCCCCCCCCCCCCCCCC(=O)NC(COP(=O)([O-])OCC[N+](C)(C)C)C(O)CCCCCCCCCCCCCCC]

As the dihydrosphingomyelin, for example, dihydrosphingomyelin obtained by reducing naturally occurring sphingomyelin by a general method may be used, or dihydrosphingomyelin obtained by synthesis may be used.

Since most dihydrosphingomyelins derived from natural products such as chicken eggs generally have two long-chain alkyl groups respectively having 16 carbon atoms, it is preferable to use dihydrosphingomyelin obtained by chemical synthesis, from the viewpoint that dihydrosphingomyelin having a long-chain alkyl group having 16 carbon atoms and a long-chain alkyl group having 18 carbon atoms can be obtained with high purity.

The ratio of dihydrosphingomyelin in the total lipids constituting the liposome is preferably 30% to 80% by mole, more preferably 40% to 70% by mole, and still more preferably 50% to 60% by mole.

The liposome according to the embodiment of the present invention contains a lipid modified with polyethylene glycol (hereinafter, referred to as a PEG-modified lipid). It is noted that as the polyethylene glycol, a derivative thereof can also be used, and examples the derivative thereof include methoxypolyethylene glycol. Hereinafter, in a case of being referred to as PEG modification, the PEG modification also applies to a derivative of polyethylene glycol.

Examples of the PEG-modified lipid include a PEG-modified phospholipid, a PEG-modified monoglyceride, a PEG-modified diglyceride, a PEG-modified sorbitan fatty acid ester, a PEG-modified monoalkyl ether, and a PEG- The liposome according to the embodiment of the present invention contains cholesterol. The addition of cholesterol to the liposome is expected to lower the fluidity of the membrane of the liposome, for example, by filling the gaps in the membrane of the liposome.

The ratio of cholesterol in the lipid constituting the liposome is preferably 20% by mole to 50% by mole, more preferably 30% by mole to 45% by mole, and still more preferably 35% by mole to 43% by mole.

(Topotecan or Salt Thereof)

The liposome according to the embodiment of the present invention encompasses topotecan or a salt thereof. The topotecan has a chemical name of (10-[(dimethylamino) methyl]-4-ethyl-4,9-dihydroxy-1H-pyrano[3',4' 6,7]indolidino[1,2-b]quinoline-3,14(4H,12H)dione and is an anti-cancer agent having an inhibitory action on topoisomerase activity. In the present invention, the topotecan may be topotecan itself or may be a salt thereof, which is acceptable as a pharmaceutical product, or it may be a prodrug that liberates topotecan in vivo. In the present invention, it is preferable to use topotecan hydrochloride.

(Ammonium Sulfate in Inner Water Phase)

The inner water phase of the liposome in the present invention contains an ammonium salt. Examples of the ammonium salt include an ammonium sulfate salt, ammonium citrate, ammonium phosphate, ammonium tartrate, ammonium succinate, ammonium fatty acid, ammonium chloride, and sucrose octasulfate as ammonium sulfate. Among them, since the retention stability of a drug can be improved by reducing the solubility of the drug in the liposome to precipitate the drug, an ammonium sulfate salt, an ammonium citrate salt, an ammonium phosphate salt, or a sucrose octasulfate as ammonium sulfate is preferable, and an ammonium sulfate salt is particularly preferable.

The molar ratio of the sulfate ions contained in the inner water phase to the molar sum of the topotecan or salt thereof contained in the treatment agent according to the embodiment of the present invention is preferably 0.36 or more preferably 0.4 or more, still more preferably 0.4 or more and 1.8 or less, and particularly preferably 0.6 or more and 1.8 or less in terms of topotecan. In a case of setting the molar ratio of sulfate ions as described above, it is possible to suppress leakage of the drug from the liposome in the blood.

In addition, in the treatment agent according to the embodiment of the present invention, the ratio of sulfate ions contained in the inner water phase of the liposome to sulfate ions of the entire treatment agent (the inner water phase ratio of the sulfate ions) is preferably at least 80% and more preferably 90% or more. At the same time, the ratio of the topotecan or salt thereof contained in the inner water phase of the liposome to the topotecan or salt thereof of the entire treatment agent (the inner water phase ratio of the drug) is preferably at least 80% and more preferably 90% or more.

The concentration of the topotecan or salt thereof in the liposome can be measured, for example, by liquid chromatography/ultraviolet-visible absorbance detection. In addition, the sulfate ions concentration in the inner water phase of the liposome can be measured, for example, by ion chromatography.

(Production Method for Liposome)

A production method for the liposome according to the embodiment of the present invention is not particularly limited; however, the production method can be carried out with reference to, for example, WO2018/181963A.

(Treatment Agent)

The present invention relates to a treatment agent for Merkel cell cancer.

Merkel cell cancer is a very rare kind of skin cancer that occurs as a result of the endless proliferation of Merkel cells present in the epidermis of the skin.

The Merkel cell cancer according to the embodiment of the present invention may be local or metastatic.

The treatment agent according to the embodiment of the present invention can be used for treating Merkel cell cancer resistant to immunotherapy.

The resistance refers to that cancer cells exhibit tolerance (resistance) to anti-cancer agents, which includes the natural resistance that anti-cancer agents do not work from the beginning of curing and a state where the effect of anti-cancer agents effective in the beginning is not exhibited as the curing is continued or the effect thereof is attenuated. Specifically, it means properties of showing no proper response to an anti-cancer agent from the viewpoint that a response to an anti-cancer agent is shown in the initial stage but responsiveness is reduced during the subsequent curing or cells continue to proliferate in the process of the curing using the anti-cancer agent.

It is important in cancer treatment to prolong the period during which a curing effect is obtained by changing the kinds of anti-cancer agents for tumors that have shown resistance. In addition, the kind and number of anti-cancer agents that have shown resistance may be the important information for the selection of the anti-cancer agent which is subsequently carried out.

Examples of the cancer suitable for curing according to the present invention include Merkel cell cancer in which pre-curing with an anti-cancer agent has not been carried out and Merkel cell cancer in which one or a plurality of kinds of pre-curing have been carried out. It is preferably Merkel cell cancer which has been subjected to 3 times or less of pre-curing or Merkel cell cancer which has shown resistance after carrying out immunotherapy, and it is particularly preferably Merkel cell cancer which has shown resistance to immunotherapy and been subjected to 3 times or less of pre-curing including 3 times or less of pre-curing with the immunotherapy.

The formulation form of the treatment agent according to the embodiment of the present invention is preferably a liquid medicinal preparation, and examples thereof include an injection agent.

The concentration of the topotecan or salt thereof contained in the liquid medicinal preparation according to the embodiment of the present invention is preferably 0.25 mg/mL to 5 mg/mL in terms of topotecan. It is more preferably 0.1 mg/mL to 3 mg/mL and still more preferably 0.5 mg/mL to 3 mg/mL.

The pH of the liquid medicinal preparation according to the embodiment of the present invention is preferably 5.5 to 8.5.

The liquid medicinal preparation according to the embodiment of the present invention generally may contain additives such as an emulsifying agent, a surfactant, a dissolution assisting agent, a suspending agent, an isotonizing agent, a buffering agent, a preservative, an antioxidant, a stabilizer, and an absorption promoting agent.

The isotonizing agent is not particularly limited. However, examples thereof include inorganic salts such as sodium chloride, potassium chloride, sodium hydrogen phosphate, sodium dihydrogen phosphate, and potassium dihydrogen phosphate; polyols such as glycerol, mannitol, and sorbitol; and sugars such as glucose, fructose, lactose, and sucrose.

The stabilizer is not limited to; however, examples thereof include sugars such as glycerol, mannitol, sorbitol, lactose, and sucrose.

The antioxidant is not particularly limited; however, examples thereof include ascorbic acid, uric acid, tocopherol homologues (for example, vitamin E and four isomers of tocopherol α, β, γ, and δ), cysteine, and EDTA. The stabilizer and the antioxidant can be each used alone or in a combination of two or more.

Examples of the pH adjusting agent include sodium hydroxide, citric acid, acetic acid, triethanolamine, sodium hydrogen phosphate, sodium dihydrogen phosphate, and potassium dihydrogen phosphate.

The liquid medicinal preparation according to the embodiment of the present invention may contain a pharmaceutically acceptable organic solvent (ethanol or the like), collagen, polyvinyl alcohol, polyvinylpyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerin, propylene glycol, polyethylene glycol, vaseline, paraffin, stearyl alcohol, stearic acid, human serum albumin (HSA), mannitol, sorbitol, lactose, PBS, sodium chloride, sugars, an in vivo degradable polymer, a serum-free medium, and an additive acceptable as a pharmaceutical additive.

The administration method for the treatment agent according to the embodiment of the present invention is preferably parenteral administration. The administration route includes routes of intravenous, intraarterial, intramuscular, intraperitoneal, subcutaneous, intraocular, and intraspinal, where a route of intravenous is preferable. Examples of the administration method include administration with a syringe or drip infusion.

The container to be filled with the liquid medicinal preparation is not particularly limited; however, it is preferably made of a material having low oxygen permeability. Examples thereof include a plastic container, a glass container, and a bag made from a laminated film.

The treatment agent according to the embodiment of the present invention can also be used in combination with another active substance or a treatment method, which is useful in treating the cancer of interest. It can be used in combination with, as the treatment method, physical curing such as radiotherapy or particle beam therapy, surgical curing such as surgery, chemotherapy, molecule targeted therapy, and cancer immunotherapy. It can be used in combination with, as the other active substance, a chemotherapeutic agent that is used in chemotherapy, a molecule targeted therapeutic drug that is used in molecule targeted therapy, a cell preparation or antibody preparation which is used in cancer immunotherapy, an immune checkpoint inhibitor. Examples of the chemotherapeutic agent include an alkylating agent, an antimetabolite, an anti-tumor antibiotic, an alkaloid, a hormone therapeutic agent, a platinum complex, a topoisomerase inhibitor, and a microtubule targeted agent.

(Dosage and Dose Rate)

It is preferable that the treatment agent according to the embodiment of the present invention is administered at a dose rate per administration of the topotecan or salt thereof encompassed in the liposome such that the dose rate is 0.1 $mg/m^2$ body surface area to 10 $mg/m^2$ body surface area in terms of topotecan. It is preferably 0.5 $mg/m^2$ body surface area to 5 $mg/m^2$ body surface area and more preferably 1.0 $mg/m^2$ body surface area to 3.5 $mg/m^2$ body surface area.

The treatment agent according to the embodiment of the present invention is preferably repeatedly administered a plurality of times of single administration every one week to eight weeks. It is more preferably repeatedly administered a plurality of times of single administration at every one week to six weeks, it is still more preferably repeatedly administered a plurality of times of single administration at every one week to four weeks, and it is particularly preferably repeatedly administered a plurality of times of single administration at every two weeks.

The treatment agent according to the embodiment of the present invention is preferably administered by infusion over 5 to 360 minutes in a single administration. 5 minutes to 240 minutes are more preferable, 10 minutes to 120 minutes are still more preferable, and 30 minutes to 120 minutes are particularly preferable.

The dose rate per administration of the topotecan or salt thereof contained in the treatment agent according to the embodiment of the present invention is, for example, preferably about 0.1 $mg/m^2$ body surface area, about 0.5 $mg/m^2$ body surface area, about 1.0 $mg/m^2$ body surface area, about 1.5 $mg/m^2$ body surface area, about 2.0 $mg/m^2$ body surface area, about 2.5 $mg/m^2$ body surface area, about 2.6 $mg/m^2$ body surface area, about 3.0 $mg/m^2$ body surface area, about 3.5 $mg/m^2$ body surface area, about 4.0 $mg/m^2$ body surface area, about 4.5 $mg/m^2$ body surface area, about 5.0 $mg/m^2$ body surface area, about 5.5 $mg/m^2$ body surface area, about 6.0 $mg/m^2$ body surface area, about 6.5 $mg/m^2$ body surface area, about 7.0 $mg/m^2$ body surface area, about 7.5 $mg/m^2$ body surface area, about 8.0 $mg/m^2$ body surface area, about 8.5 $mg/m^2$ body surface area, about 9.0 $mg/m^2$ body surface area, about 9.5 $mg/m^2$ body surface area, or about 10 $mg/m^2$ body surface area in terms of topotecan. It is more preferably about 0.5 $mg/m^2$, about 1.0 $mg/m^2$ body surface area, about 1.5 $mg/m^2$ body surface area, about 2.0 $mg/m^2$ body surface area, about 2.5 $mg/m^2$ body surface area, about 2.6 $mg/m^2$ body surface area, about 3.0 $mg/m^2$ body surface area, about 3.5 $mg/m^2$ body surface area, or about 5.0 $mg/m^2$ body surface area, still more preferably about 1.0 $mg/m^2$ body surface area, about 1.5 $mg/m^2$ body surface area, about 2.0 $mg/m^2$ body surface area, about 2.5 $mg/m^2$ body surface area, about 2.6 $mg/m^2$ body surface area, about 3.0 $mg/m^2$ body surface area, or, about 3.5 $mg/m^2$ body surface area, and particularly preferably about 1.0 $mg/m^2$ body surface area, about 1.5 $mg/m^2$ body surface area, about 2.0 $mg/m^2$ a body surface area, about 2.5 $mg/m^2$ body surface area, about 2.6 $mg/m^2$ body surface area, or about 3.5 $mg/m^2$ body surface area.

EXAMPLES

The present invention will be described in more detail below according to Examples; however, the present invention is not limited to these Examples.

<Preparation of Liquid Medicinal Preparation Containing Topotecan-Encompassing Liposome>

With reference to WO2018/181963A, a liquid medicinal preparation (hereinafter, referred to as an A preparation) containing topotecan-encompassing liposomes having the following composition was prepared.

| | |
|---|---|
| Topotecan hydrochloride | 3.0 mg/mL (6.5 mmol) |
| DHSM (see note 1) | 10.4 mg/mL |
| DSPE-MPEG2000 (see note 2) | 3.6 mg/mL |
| Cholesterol | 3.6 mg/mL |
| Ammonium sulfate | 0.9 mg/mL (6.9 mmol) |
| Sucrose | appropriate amount |
| L-histidine | appropriate amount |
| Sodium chloride | appropriate amount |
| Water (solvent) | appropriate amount |

(Note 1)
Dihydrosphingomyelin prepared by chemical synthesis so that a content of a compound 1 having a long-chain alkyl group having 16 carbon atoms and a long-chain alkyl group having 18 carbon atoms is 98% or more.
(Note 2)
1,2-distearoyl-sn-glycero-3-phosphoethanolamine-N-(methoxy(polyethylene glycol)-2000)

<Physical Property Value of a Preparation>

The pH of the A preparation was 7.4, and the particle diameter of the liposome contained in the A preparation was 91 nm in terms of the cumulant average particle diameter. In addition, the molar ratio of the sulfate ions contained in the inner water phase to the topotecan hydrochloride was 1.05.

Reference Example 1: Prediction of Suitable Dose in Human from Non-Clinical Test The A preparation was diluted with a 5% glucose solution to 0.1, 0.2, and 0.4 mg/mL, and 15 male and 15 female SD rats (Charles River Laboratories Japan, Inc.) (30 rats in total) were subjected to intravenous administration at a dose of 0.5, 1, and 2 mg/kg (respectively, 3, 6, and 12 $mg/m^2$) 4 times (4 weeks) at an interval of once a week, where a TK group (12 males and 12 females) was set for each group.

In the group at a dose of 1 mg/kg or less, there was no death due to the A preparation during the test period. It is noted that the toxicity target organs of the A preparation were a hematopoietic system, a lymphatic system, and a digestive system.

Those in the group at a dose of 2 mg/kg were found in a dead state or sacrificed in extremis during the administration period and the day after the completion of the administration.

In the group in which the dose of the A preparation was 1 mg/kg or more, hemorrhage and decrease of neutrophils due to the dose rate-responsive myelosuppression were observed. In addition, the decrease of lymphocytes, the lymphocyte depletion in the spleen, the thymus, and the lymph nodes, and the necrosis of the gastrointestinal epithelium, as well as the hyperplasia of the intestinal crypt and the depletion of hematopoietic cells in the bone marrow were observed, which were conceived to be changes that occurred in response to the cell growth inhibitory effect of the A preparation. All of these changes showed recoverability after a recovery period of 4 weeks. On the other hand, in the group at a dose of 0.5 mg/kg, the change due to the A preparation was not observed.

Based on the above results, the maximum tolerated dose rate in a rat was set to 1 mg/kg (6 $mg/m^2$) at which no death is observed, and the initial dose rate in a human was set to 1.0 $mg/m^2$, which is about 1/10 of the maximum tolerated dose rate.

Reference Example 2: Relationship Between Toxicity and Blood Kinetics (Toxicokinetics)

In a case where 1 mg/kg, which is the maximum tolerated dose rate of the A preparation obtained in Reference Example 1, was intravenously administered to a rat, the total topotecan exposure in the blood plasma was 28,400 ng/mL (Cmax) and 563,000 h·ng/mL ($AUC_{0-96}$), and the exposure in a case of administration at 0.5 mg/kg, at which no toxicity was observed, was 11,000 ng/mL (Cmax) and 491,000 h·ng/mL ($AUC_{0-96}$).

Reference Example 3: Temporal Change of Toxicity Profile after Administration The A preparation was diluted with a 5% glucose solution to 0.05, 0.1, and 0.2 mg/mL, and 6 male SD rats (Charles River Laboratories Japan, Inc.) were each subjected to single intravenous administration at a dose of 0.25, 0.5, and 1 mg/kg (respectively, 1.5, 3, and 6 $mg/m^2$). Blood was collected at 1, 3, 5, 7, 10, 14, and 21 days after the administration, and a hematological test, a feeding amount measurement, and a body weight measurement were carried out. It is noted that no dead case or moribund case was observed at all dose rates.

In the group at a dose of 1 mg/kg, the low values of the erythroid system and the leukocyte system were observed until 14 days after the administration, which tended to recover from 10 days after the administration. The suppression of the body weight increase was observed until 5 days after the administration, which was recovered 10 days after the administration.

In the group at a dose of 0.5 mg/kg or less, any change was slight as compared with the group at a dose of 1 mg/kg, and the recovery was rapid.

From the above, it was found that in a case where a rat is subject to a single intravenous administration of 1 mg/kg, changes in the hematopoietic system, the lymphatic system, and the digestive system, which are the toxicity target organs of the A preparation, are recovered on the 14th day of the administration.

Reference Example 4: Prediction of Suitable Administration Schedule in Human from Non-Clinical Test Based on the rat toxicokinetics (TK) data obtained in Reference Example 2, the total topotecan exposure of the A preparation in a human was calculated using population pharmacokinetics (PPK).

As a result of calculating the clearance of the total topotecan per body weight based on the PPK model, it was 1.86 mL/h/kg (rat). As a result of fitting the clearance in a human with exponentiation with the body weight as a base according to the $CL=a*BW^b$, the clearance in a human was calculated to be 113 mL/h or 1.61 mL/h/kg in terms of body weight in a patient having a body weight of 70 kg. The predicted value of the clearance was 100 times lower than 18.6 L/hr which is a clearance in a case where topotecan is intravenously administered (reference document: Mould et al., 2002, Ait-Oudhia, Mager and Straubinger 2014).

Using the clearance in a human calculated in the PPK model, a simulation was carried out in a case where the A preparation was administered to a human once every two weeks at a dose from 1 to 12 $mg/m^2$, and as a result, $t_{1/2}$ of the total topotecan was 18.5 hours (90% reliability interval: 13.2 to 24.6 hours), which was 9 times longer than the clearance in a case where topotecan is intravenously administered (reference document: HYCAMTIN, attached document). There was no accumulation and a steady state was observed in a case of being administered once every two weeks between 1 and 12 $mg/m^2$.

From the above results, it was predicted to be suitable to administer the A preparation once every two weeks due to the decrease in clearance due to liposomization and the extension of $t_{1/2}$. In addition, in the rat test of Reference Example 3, it was confirmed that the change due to the toxicity is recovered 2 weeks after the administration, and from this viewpoint as well, it was predicted that the administration once every two weeks is suitable.

Example: Administration Test

Based on the dose predicted from Reference Example 1, the A preparation was used in the curing shown in Examples 1 and 2 below. It is noted that the curing was carried out at Honor Health Research Institute located in Scottsdale, Arizona, USA, Sarah Cannon Research Institute located in Denver, Colorado, USA, University of Texas, M.D. Anderson Cancer Center, located in Houston, Texas, USA, and Dana Farber Cancer Institute located in Boston, Massachusetts, USA.

The drug administration cycle of administering the A preparation to a cancer patient once every two weeks was repeated. Specifically, 28 days were set as one cycle, the A preparation was administered on the 1st day and the 15th day, and the cycle consisting of these 28 days was repeated.

The curing effect was determined according to the following criteria.

The subject to be evaluated was checked by image diagnosis by computed tomography (CT) or magnetic resonance imaging (MRI), and the evaluation was made according to the following criteria.

Complete response (CR): A state in which the tumor is completely disappeared.

Partial response (PR): A state in which the size of the tumor is reduced by 30% or more as compared with the sum of the sizes of the tumor before drug administration.

Progressive disease (PD): A state in which the size of the tumor is increased by 20% or more and the absolute value thereof is increased by 5 mm or more as compared with the sum of the sizes of the smallest tumor during the progress, or a state in which a new lesion has appeared.

Stable disease (SD): A state in which there is no reduction corresponding to PR and no increase corresponding to PD as compared with the sum of the sizes of the smallest tumors during the progress.

It is noted that since the purpose of chemotherapy for solid cancer is to relieve symptoms and prolong life, it is determined to be effective as a drug effect even in a case where the curing effect is SD.

1. Merkel Cell Cancer Patient

In a Merkel cell cancer patient to which the A preparation was administered at 2.0 $mg/m^2$ in terms of topotecan per administration, PR was confirmed, and the curing was continued for about 32 weeks.

This patient had received, as pre-curing, drug therapy with a single agent of pembrolizumab and enapotamab vedotin. The patient was 62 years old and was male.

An excellent preventive or curing effect on the Merkel cell cancer was obtained from the treatment agent according to the embodiment of the present invention. Specifically, the effect is an effect of reducing the volume of the Merkel cell cancer or an effect of not changing the size of the Merkel cell cancer. From these results, the treatment agent according to the embodiment of the present invention is expected to prolong the progression-free survival time and the overall survival time of patients, and it has a very useful effect from the viewpoint of improving the QOL of patients.

The curing effect on the Merkel cell cancer patient was confirmed according to image diagnosis by CT. The results are shown in FIG. 1. a of FIG. 1 is a baseline image before the administration of the A preparation. b of FIG. 1 is a CT image in a case where PR was confirmed 8 weeks after the administration. c of FIG. 1 is a CT image in a case where it is confirmed that PR is continued after 16 weeks have passed from the administration. As shown in FIG. 1, the A preparation exhibits a very excellent effect in the curing of the Merkel cell cancer.

What is claimed is:

1. A treatment method for Merkel cell cancer, comprising:

a step of administering a composition comprising a liposome comprising an inner water phase and an aqueous solution which is an outer water phase in which the liposome is dispersed, wherein the liposome encompasses topotecan or a salt thereof, a lipid constituting the liposome comprises a lipid modified with polyethylene glycol, dihydrosphingomyelin, and cholesterol, and the inner water phase contains an ammonium salt, wherein topotecan or the salt thereof encompassed in the liposome is administered at a dose rate of 0.1 $mg/m^2$ body surface area to 3.5 $mg/m^2$ body surface area, in terms of topotecan per administration, wherein administration is repeated every two weeks.

2. The treatment method according to claim 1, wherein the dihydrosphingomyelin is dihydrosphingomyelin comprising an alkyl group comprising 16 carbon atoms and an alkyl group comprising 18 carbon atoms.

3. The treatment method according to claim 1, wherein the ammonium salt is ammonium sulfate, and a molar ratio of sulfate ions contained in the inner water phase to the molar sum of the topotecan or the salt thereof contained in the treatment agent is 0.36 or more in terms of topotecan.

4. The treatment method according to claim 1, wherein the lipid modified with polyethylene glycol is diacylphosphatidylethanolamine modified with polyethylene glycol or methoxypolyethylene glycol.

5. The treatment method according to claim 1, wherein a formulation ratio of the cholesterol to a total of the lipid constituting the liposome is 35% to 43% by mole.

6. The treatment method according to claim 1, wherein a pH of the outer water phase is 5.5 to 8.5.

7. The treatment method according to claim 1, wherein an administration route is an intravenous administration.

* * * * *